(12) United States Patent
Refaai

(10) Patent No.: US 11,940,445 B2
(45) Date of Patent: Mar. 26, 2024

(54) ABO BLOOD GROUP POINT-OF-CARE TESTING

(71) Applicant: UNIVERSITY OF ROCHESTER, Rochester, NY (US)

(72) Inventor: Majed Refaai, Henrietta, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 498 days.

(21) Appl. No.: 17/045,330

(22) PCT Filed: Apr. 5, 2019

(86) PCT No.: PCT/US2019/026037
§ 371 (c)(1),
(2) Date: Oct. 5, 2020

(87) PCT Pub. No.: WO2019/195710
PCT Pub. Date: Oct. 10, 2019

(65) Prior Publication Data
US 2021/0373007 A1     Dec. 2, 2021

Related U.S. Application Data

(60) Provisional application No. 62/654,118, filed on Apr. 6, 2018.

(51) Int. Cl.
    *G01N 33/543*     (2006.01)
    *G01N 33/80*     (2006.01)

(52) U.S. Cl.
    CPC ....... *G01N 33/54373* (2013.01); *G01N 33/80* (2013.01)

(58) Field of Classification Search
USPC ............ 422/546; 436/172; 435/287.1, 286.2
See application file for complete search history.

(56) References Cited

U.S. PATENT DOCUMENTS

| | | | |
|---|---|---|---|
| 4,178,071 A * | 12/1979 | Asbell | A61M 5/3129 D16/135 |
| 9,686,395 B2 * | 6/2017 | Erickson | G01N 21/31 |
| 10,857,301 B2 * | 12/2020 | Loonan | A61M 5/31571 |
| 2009/0170062 A1 | 7/2009 | Schwind | |
| 2010/0112723 A1 | 5/2010 | Battrell | |

(Continued)

FOREIGN PATENT DOCUMENTS

| | | | |
|---|---|---|---|
| DE | 19713249 A1 * | 10/1998 | ............ B01L 3/502 |
| DE | 10311731 | 10/2003 | |

(Continued)

OTHER PUBLICATIONS

Malomgre et al (Recent and future trends in blood group typing, Anal Bioanal Chem (2009) 393:1443-1451) (Year: 2009).*

(Continued)

*Primary Examiner* — Ann Montgomery
*Assistant Examiner* — Chau N. B. Tran
(74) *Attorney, Agent, or Firm* — Riverside Law LLP

(57) ABSTRACT

The present invention provides point-of-care blood typing devices. The devices require only a small sample of blood and are able to provide results within minutes. The devices are capable of identifying A, B, AB, and O type blood. The devices are also capable of identifying blood that is positive (+) or negative (−) for the D antigen.

17 Claims, 17 Drawing Sheets

(56) References Cited

U.S. PATENT DOCUMENTS

| | | | |
|---|---|---|---|
| 2013/0017623 A1* | 1/2013 | Wu | A61B 10/0051 422/69 |
| 2016/0206818 A1* | 7/2016 | Berend | A61M 5/3129 |
| 2018/0256818 A1* | 9/2018 | Lümkemann | A61M 5/284 |
| 2021/0102962 A1 | 4/2021 | Refaai | |

FOREIGN PATENT DOCUMENTS

| | | | |
|---|---|---|---|
| KR | 20170006981 | * | 2/2015 |
| TW | 201336537 | * | 3/2012 |
| WO | 8603008 | | 5/1986 |
| WO | 9009596 | | 8/1990 |
| WO | 2013083619 | | 6/2013 |

OTHER PUBLICATIONS

Lilly (Disposable Insulin Delivery Device User Manual, 2005). (Year: 2005).*

Ashiba, Hiroki, et al. "Microfluidic chips for forward blood typing performed with a multichannel waveguide-mode sensor." Sensing and bio-sensing research 7 (2016): 121-126.

Chen, Jun-You, et al. "Rapid and inexpensive blood typing on thermoplastic chips." Lab on a Chip 15.24 (2015): 4533-4541.

Li, Miaosi, et al. "Paper-Based blood typing device that reports patient's blood type "in writing"." Angewandte Chemie 124.22 (2012): 5593-5597.

Zhang, Hong, et al. "A dye-assisted paper-based point-of-care assay for fast and reliable blood grouping." Science translational medicine 9.381 (2017): eaaf9209.

Karimi, Shadi, et al. "A passive portable microfluidic blood-plasma separator for simultaneous determination of direct and indirect ABO/Rh blood typing." Lab on a Chip 19.19 (2019): 3249-3260. (Year: 2019).

Wessel, Lindzi. "Watch a Special Paper Tool That Can Determine Your Blood Type in Seconds." Science, American Association for the Advancement of Science, Mar. 15, 2017, www.science.org/content/article/watch-special-paper-tool-can-determine-your-blood-type-seconds. Accessed Sep. 25, 2023. 4 pages.

* cited by examiner

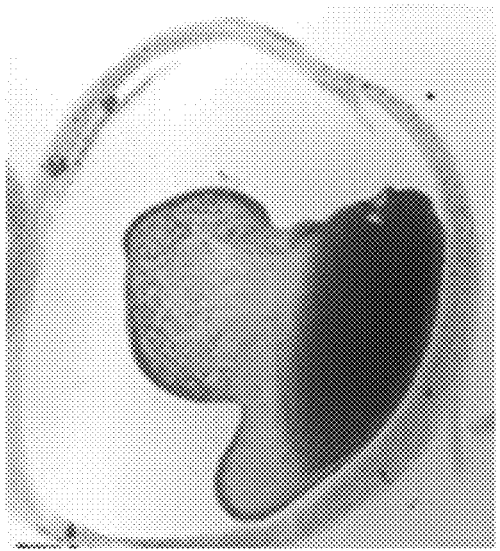
FIG. 8A
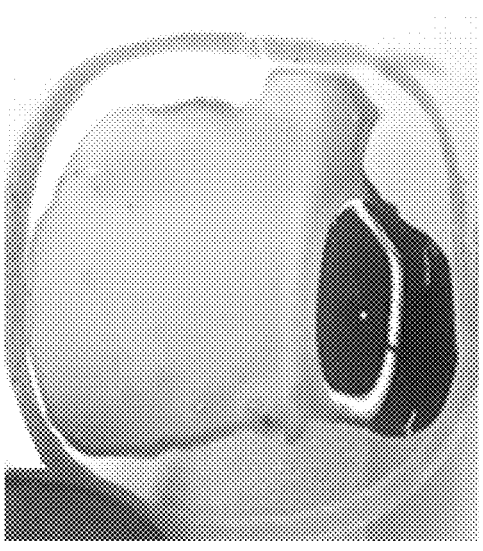
FIG. 8B
FIG. 8C
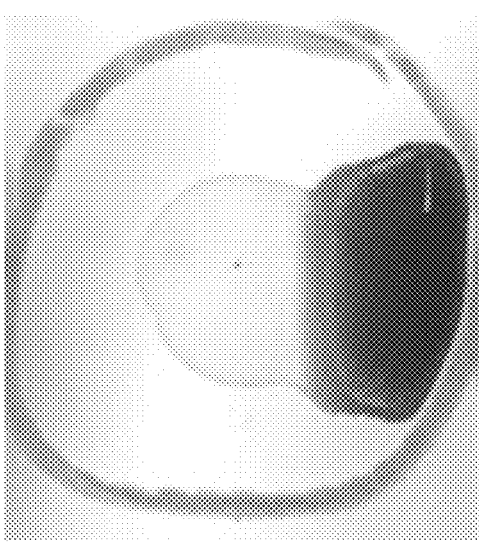
FIG. 8D
FIG. 8A – FIG. 8D

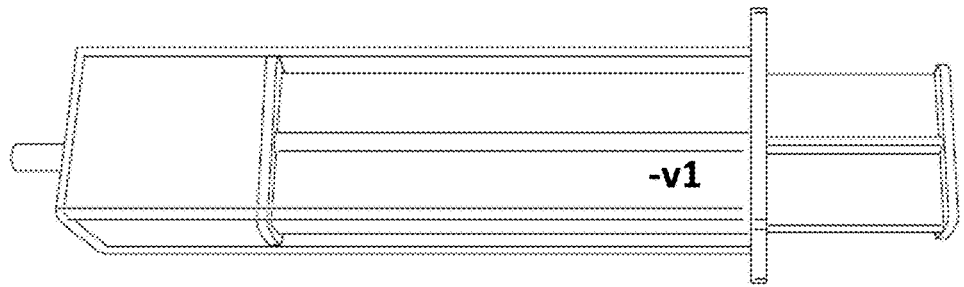
FIG. 10D
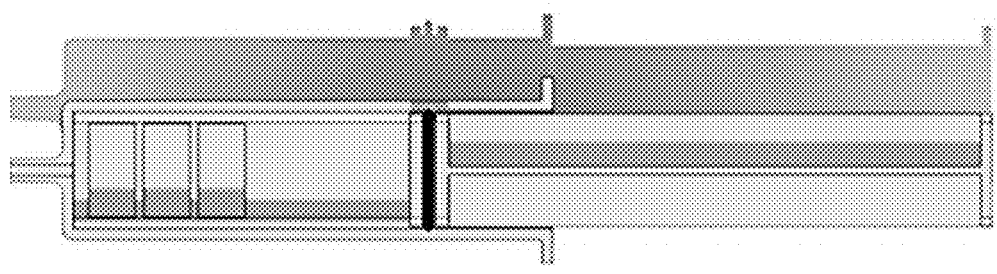
FIG. 10C
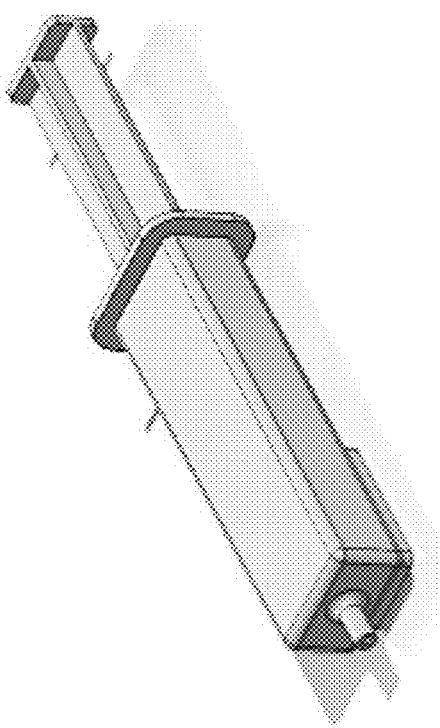
FIG. 10A
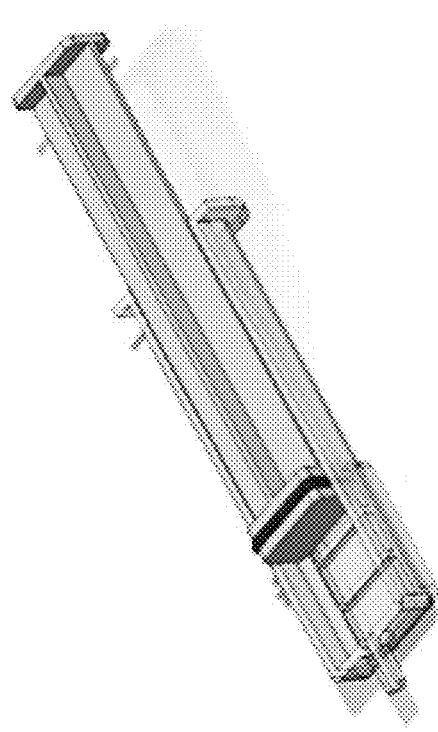
FIG. 10B
FIG. 10A – FIG. 10D

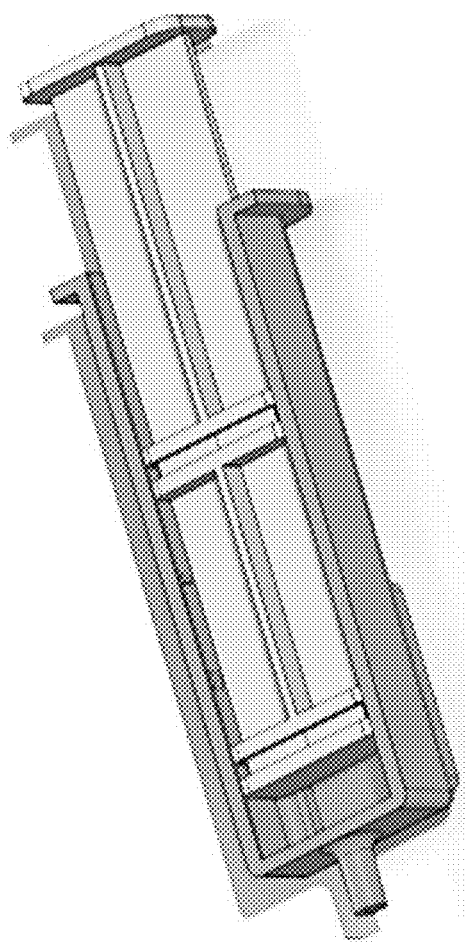
FIG. 11A
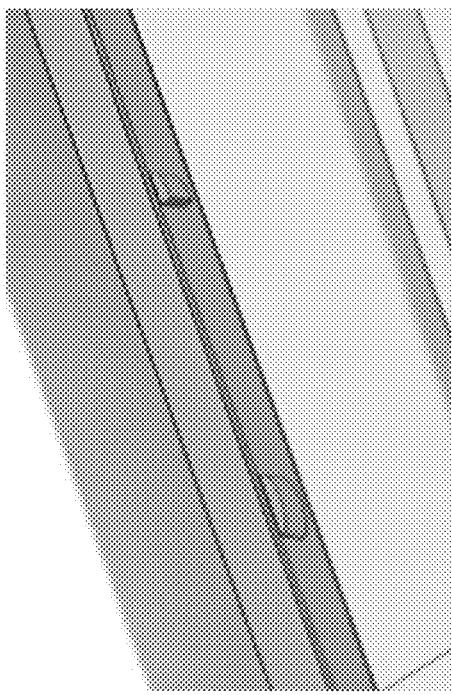
FIG. 11C
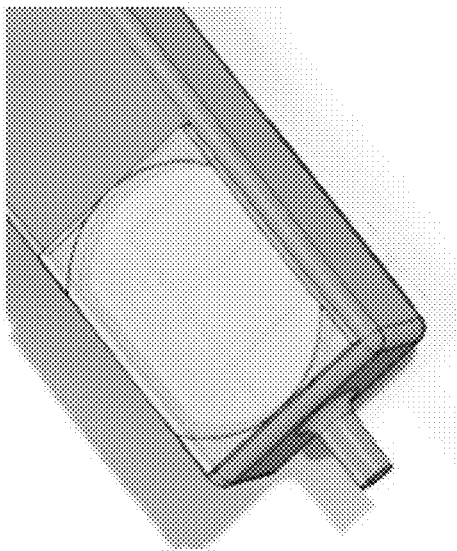
FIG. 11B
FIG. 11A – FIG. 11C

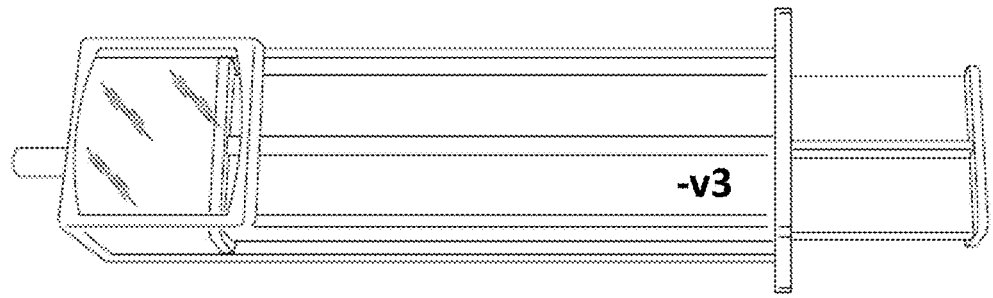
FIG. 12D
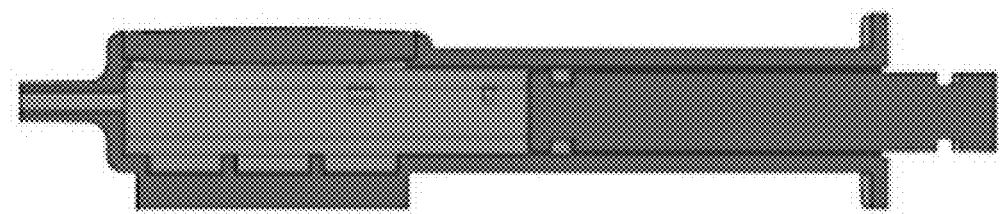
FIG. 12C
FIG. 12A – FIG. 12D
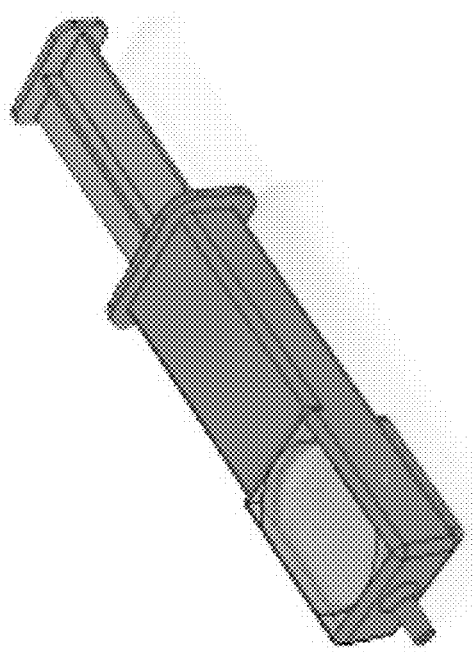
FIG. 12A
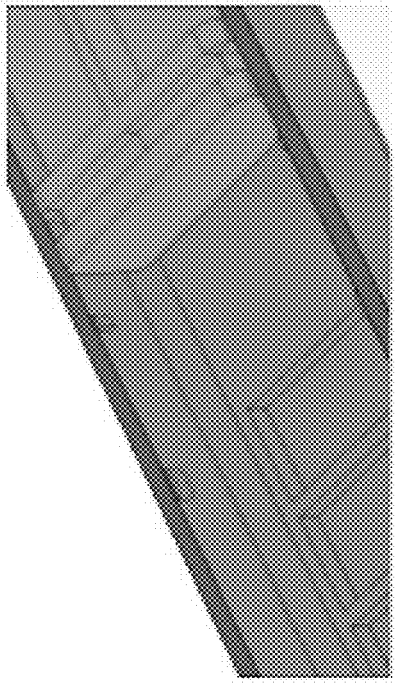
FIG. 12B FIG. 13A
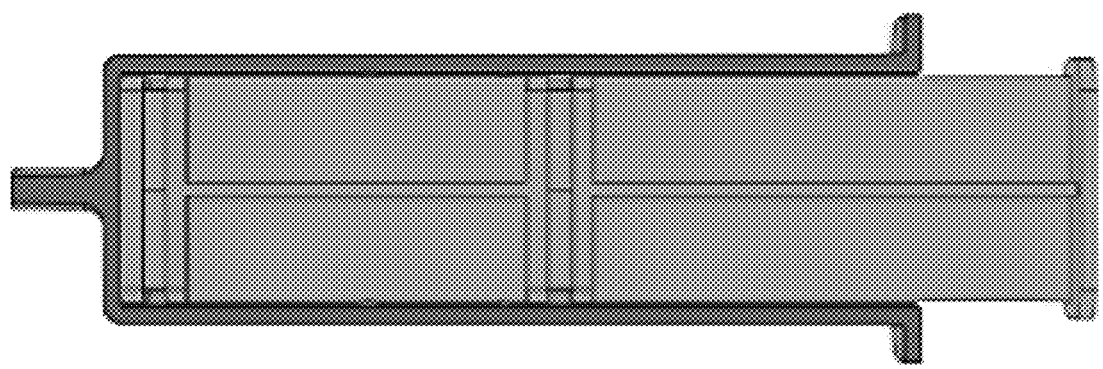
FIG. 13B
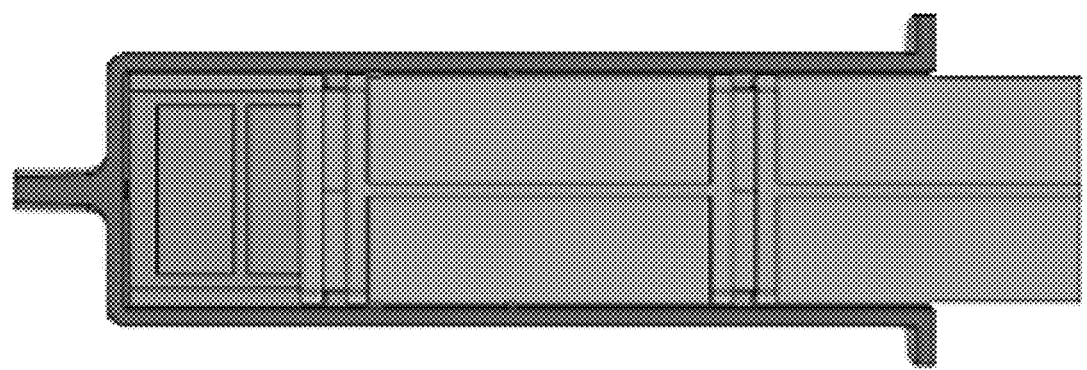
FIG. 13C
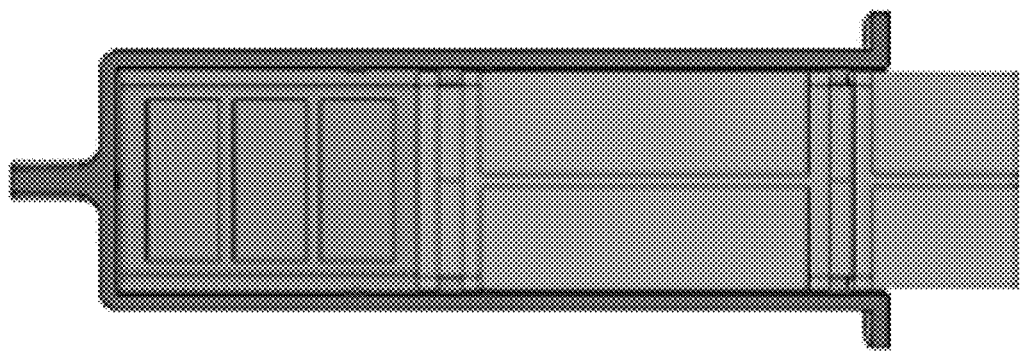
FIG. 13A – FIG. 13C FIG. 15A
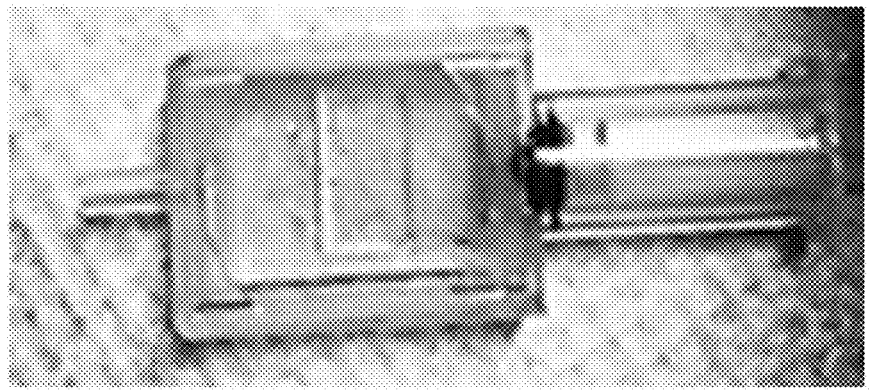
FIG. 15B
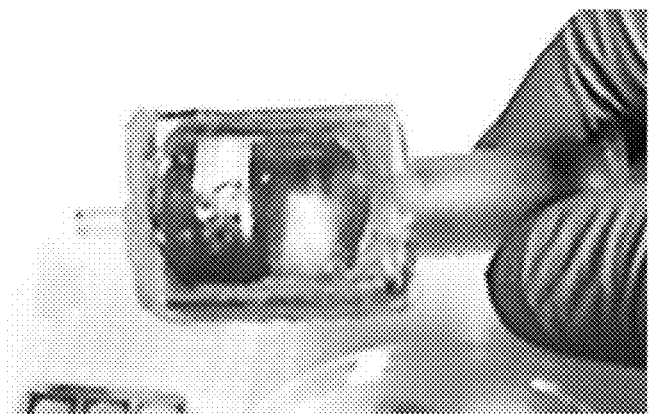
FIG. 15C
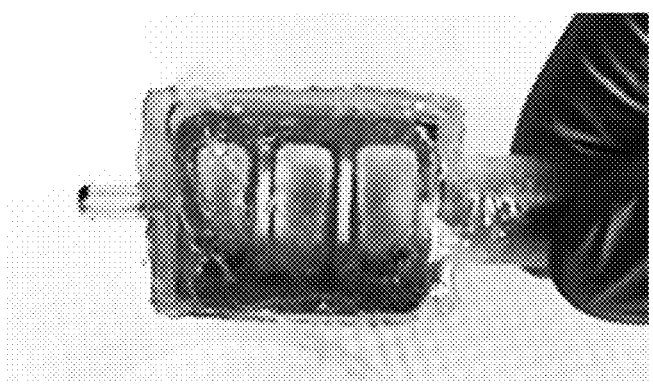
FIG. 15A – FIG. 15C

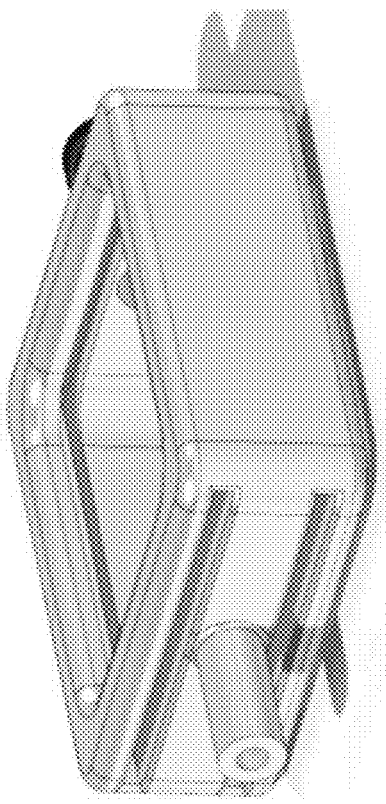
FIG. 16B
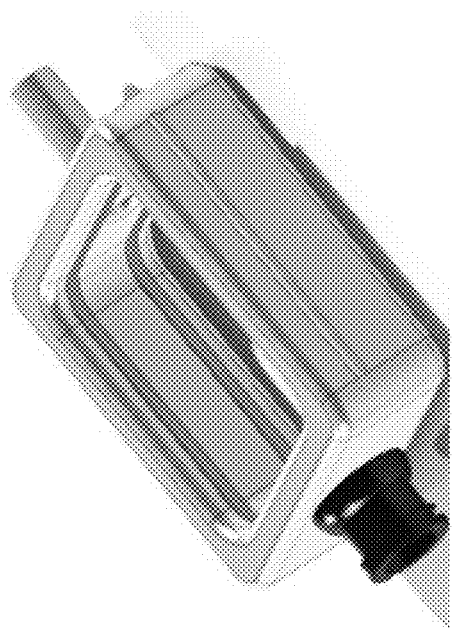
FIG. 16A
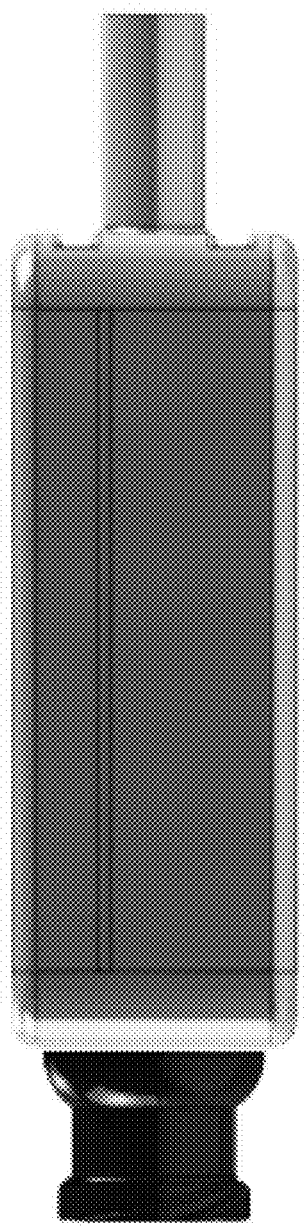
FIG. 16C
FIG. 16A – FIG. 16C

ABO BLOOD GROUP POINT-OF-CARE TESTING

CROSS-REFERENCE TO RELATED APPLICATIONS

This application is a U.S. national phase application filed under 35 U.S.C. § 371 claiming benefit to International Patent Application No. PCT/US2019/026037, filed Apr. 5, 2019, which is entitled to priority under 35 U.S.C. § 119(e) to U.S. Provisional Patent Application No. 62/654,118, filed Apr. 6, 2018, each of which application is hereby incorporated herein by reference in its entirety.

BACKGROUND OF THE INVENTION

The principle of the blood group system (also known as the ABO system) is the presence or absence of specific antigens that are physically exposed on the red blood cell (RBC) membrane. Two main antigens play an important role in differing blood groups in humans, the A and B antigens. Depending on gene expression, individuals exposing either antigen are marked as group "A" or group "B", respectively; individuals exposing both antigens are identified as group "AB"; and individuals missing both antigens are known as group "O". The carbohydrate structure of antigen A and B are slightly different, which stimulates antibody formation to the missing antigen or antigens early in life. Thus, individuals of group "A", for instance, will have anti-B antibodies circulating in their plasma, and vice versa for individuals of group "B". While individuals of group "AB" exhibit neither antibody, group "O" individuals develop both antibodies.

Identification of the ABO group system is essential in blood transfusions since exposure to inappropriate antibodies can cause acute RBC hemolysis that may lead to significant consequences, such as acute renal failure and death. ABO group identification is simple and can be performed within 20-25 minutes in the presence of adequate laboratory techniques. However, such a delay in management of acutely bleeding patients may be significantly harmful. Therefore, administration of group "O" RBCs (so-called "universal donor") until the patient's ABO group is identified is a common transfusion practice worldwide.

While administration of group "O" RBCs to all trauma patients is a presumably safe practice, the amount of anti-A and anti-B antibodies administered with each unit (30-70 mL of plasma) can cause RBC hemolysis of any non-group "O" patients (about 50-55% of the U.S. population). Significant complications have been reported following administration of the O group RBCs to non-O group recipients. This is usually due to the anti-A and anti-B antibodies present in the plasma included in the RBC unit and their interactions with A or B antigens present on the RBC membrane. Furthermore, anti-AB antibodies can also form immune complexes with the circulating soluble A and B antigens that can further contribute to considerable harm of different tissue in addition to RBC hemolysis.

Early identification of a patient's blood group will allow ABO identical transfusion and reduce exposure to anti-AB antibodies and formation of harmful immune complexes. Of note, in addition to the ABO group, the presence or absence of another antigen that only exists on the RBC membrane, known as the "D" antigen, is very essential in blood transfusion.

There is a need in the art for an improved point-of-care blood typing device. The present invention meets this need.

SUMMARY OF THE INVENTION

In one aspect, the present invention relates to a portable blood typing device comprising: an enclosure having a proximal end, a distal end, and a hollow interior; an actuatable plunger positioned within the enclosure, the plunger dividing the hollow interior into a first distal chamber and a second proximal chamber; a closeable aperture on the distal end of the enclosure providing access to the first chamber; and at least one well embedded in the enclosure; wherein the at least one well comprises a first surface region coated in a first probe that binds to antigen A, a second surface region coated in a second probe that binds to antigen D, and a third surface region coated in a third probe that binds to antigen B.

In one embodiment, the first probe is anti-A antibody, the second probe is anti-D antibody, and the third probe is anti-B antibody. In one embodiment, the at least one well extends outward from the first chamber such that actuation of the plunger within the enclosure does not touch the first surface region, the second surface region, or the third surface region of the at least one well. In one embodiment, the enclosure comprises at least one hard stop or detent on its inner surface that stops the plunger in at least a first distal position and at least a second proximal position. In one embodiment, the enclosure is at least partially transparent.

In one embodiment, the device further comprises a magnifying lens positioned on the enclosure opposite from the at least one well, the magnifying lens capable of magnifying the first surface region, the second surface region, and the third surface region. In one embodiment, the enclosure is at least partially squeezable. In one embodiment, the device further comprises a light source positioned on the enclosure adjacent to the at least one well, the light source capable of projecting light through the first surface region, the second surface region, and the third region, and onto a translucent surface positioned opposite from the at least one well.

In one embodiment, the device further comprises at least one side chamber fluidly connected to the hollow interior of the enclosure, the fluid connection being positioned near the proximal end of the enclosure. In one embodiment, the enclosure can split into at least two pieces, such that the plunger and the second chamber are separable from the first chamber.

In one embodiment, the device further comprises a blood typing chart attached to the enclosure, the blood typing chart relating a positive or a negative reading in the first surface region, the second surface region, and the third surface region to a blood type.

In one embodiment, the device further comprises a sensor electronically connected to a CPU and a display, wherein the sensor automatically detects a positive or negative signal on each of the surface region, the CPU assigns a blood type based on the detected signals, and the display shows the blood type. In one embodiment, the sensor is selected from the group consisting of: a light sensor, an impedance sensor, and a color sensor. In one embodiment, the sensor is readable by a smartphone.

In another aspect, the present invention provides a method of blood typing, comprising the steps of: providing the portable blood typing device of the present invention; actuating the plunger in a proximal direction to draw an amount of a blood sample into the first chamber and the at least one well; agitating the blood sample within the first chamber and the at least one well; actuating the plunger in a distal direction to eject the blood sample from the first chamber; and recording the presence of agglutination in the first surface region, the second surface region, and the third surface region.

In one embodiment, the presence of agglutination in the first surface region and the absence of agglutination in the third surface region indicates that the blood sample comprises A-type blood. In one embodiment, the absence of agglutination in the first surface region and the presence of agglutination in the third surface region indicates that the blood sample comprises B-type blood. In one embodiment, the presence of agglutination in the first surface region and the presence of agglutination in the third surface region indicates that the blood sample comprises AB-type blood. In one embodiment, the absence of agglutination in the first surface region and the absence of agglutination in the third surface region indicates that the blood sample comprises O-type blood.

In one embodiment, the presence of agglutination in the second surface region indicates that the blood sample comprises Rh positive blood. In one embodiment, the absence of agglutination in the second surface region indicates that the blood sample comprises Rh negative blood. In one embodiment, the step of recording the presence of agglutination in the first surface region, the second surface region, and the third surface region is performed by a smartphone.

In another aspect, the present invention relates to a portable blood typing device comprising: an enclosure having a proximal end, a distal end, and an aperture; one or more proximal capillary tubes within the enclosure, each capillary tube fluidly connected to the aperture at a first end and fluidly connected to a well at a second end; and a distal capillary tube fluidly connected to each well at a first end; wherein at least one well comprises a first surface region coated in a first probe that binds to antigen A, at least one well comprises a second surface region coated in a second probe that binds to antigen D, and at least one well comprises a third surface region coated in a third probe that binds to antigen B.

In one embodiment, the first probe is anti-A antibody, the second probe is anti-D antibody, and the third probe is anti-B antibody. In one embodiment, the enclosure is at least partially transparent.

In one embodiment, a removable barrier is positioned between each well and each distal capillary tube. In one embodiment, the device further comprises a barrier breaking component configured to remove the barrier by breaking the barrier, sliding the barrier, or opening an aperture in the barrier. In one embodiment, the device further comprises at least one indicator well positioned distal to the barrier breaking component, the at least one indicator well being fluidly connected to the aperture by a proximal capillary tube.

In another aspect, the present invention relates to a method of blood typing, comprising the steps of: providing the portable blood typing device of the present invention; depositing a blood sample into the aperture; flowing the blood sample into each of the wells connected to a proximal capillary tube; agitating the blood sample within each of the wells; removing the barrier between each of the wells and each of the distal capillary tubes; and recording the presence of fluid in each of the distal capillary tubes.

In one embodiment, the absence of fluid in a distal capillary tube fluidly connected to a well having a first probe indicates that the blood sample comprises A-type blood. In one embodiment, the absence of fluid in a distal capillary tube fluidly connected to a well having a third probe indicates that the blood sample comprises B-type blood. In one embodiment, the absence of fluid in a distal capillary tube fluidly connected to a well having a first probe and in a distal capillary tube fluidly connected to a well having a third probe indicates that the blood sample comprises AB-type blood. In one embodiment, the presence of fluid in a distal capillary tube fluidly connected to a well having a first probe and in a distal capillary tube fluidly connected to a well having a third probe indicates that the blood sample comprises O-type blood.

In one embodiment, the absence of fluid in a distal capillary tube fluidly connected to a well having a second probe indicates that the blood sample comprises Rh positive blood. In one embodiment, the presence of fluid in a distal capillary tube fluidly connected to a well having a second probe indicates that the blood sample comprises Rh negative blood. In one embodiment, the step of recording the presence of fluid in each of the distal capillary tubes is performed by a smartphone.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

In FIG. 2A, the plunger is drawn to the first stop to fill the device with an amount of a sample. In FIG. 2B, the plunger is drawn to the second stop to introduce an amount of air into the device to permit agitation of the sample.

In FIG. 5A, an amount of a sample is first drawn into the device. In FIG. 5B, after agitating the sample in the device, the plunger is drawn to permit the sample to enter the side chambers of the device. In FIG. 5C, the plunger is replaced in its starting position, thereby sealing the sample within the side chambers.

FIG. 7A depicts a top-down view of an exemplary blood typing device having capillary tubes. FIG. 7B depicts a top-down view of an exemplary blood typing device with a barrier breaker component attached. FIG. 7C depicts a top-down view of an exemplary blood typing device inserted into a reading device.

FIG. 8A through FIG. 8D depict the results of experiments demonstrating the binding characteristics of various surface regions. FIG. 8A and FIG. 8B depict positive signals indicated by agglutination of RBCs. FIG. 8C and FIG. 8D depict negative signals indicated by the absence of agglutination.

FIG. 10A through FIG. 10D depict an exemplary prototype blood typing device. Computer-aided design models of the prototype device are shown in FIG. 10A (perspective view), FIG. 10B (perspective cross-sectional view), and FIG. 10C (top-down cross-sectional view). FIG. 10D is a 3D resin-printed model of the prototype device.

FIG. 11A through FIG. 11C depict an exemplary prototype blood typing device having a double-sealed plunger, magnifying lens, and stop bumps/detents. Computer-aided design models of the prototype device are shown in FIG. 11A (perspective cross-sectional view), FIG. 11B (magnified view of the magnifying lens), and FIG. 11C (magnified view of the stop bumps/detents).

FIG. 12A through FIG. 12D depict an exemplary prototype blood typing device having a double-sealed plunger, magnifying lens, and stop bumps/detents. Computer-aided design models of the prototype device are shown in FIG. 12A (perspective view), FIG. 12B (magnified view of the stop bumps/detents), and FIG. 12C (side cross-sectional view). FIG. 12D is a 3D printed model of the prototype device.

FIG. 13A through FIG. 13C depict the positioning of the plunger based on the stop bumps/detents of an exemplary prototype blood typing device. FIG. 13A shows a first position of the plunger. FIG. 13B shows a second position of the plunger. FIG. 13C shows a third position of the plunger.

FIG. 14D is a 3D printed model of the prototype device shell with plunger.

FIG. 15A through FIG. 15C depict an exemplary prototype blood typing device. FIG. 15A shows the prototype device having a syringe attached to an enclosure and a magnifying lens attached to the top of the enclosure. FIG. 15B shows the prototype device with a sample of blood drawn into the enclosure using the syringe. FIG. 15C shows the prototype device with the sample of blood removed, leaving behind binding patterns on its surface regions.

FIG. 16A through FIG. 16C depict an exemplary compact prototype blood typing device. Computer-aided design models of the prototype device are shown in FIG. 16A (perspective view), FIG. 16B (perspective view), and FIG. 16C (side view).

DETAILED DESCRIPTION

The present invention provides point-of-care blood typing devices and methods of use. The devices require only a small sample of blood and are able to provide results within minutes. The devices are capable of identifying A, B, AB, and O type blood. The devices are also capable of identifying blood that is positive (+) or negative (−) for the D antigen.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Blood Typing Device

Figure 1A:
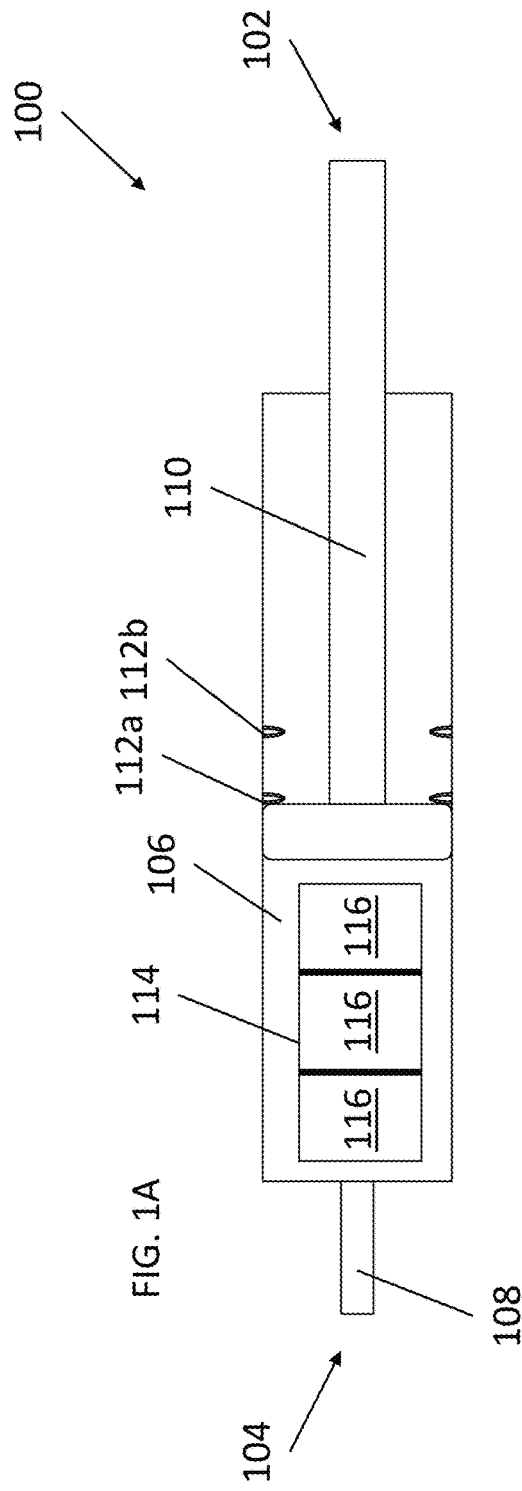
FIG. 1A depicts a top-down view of an exemplary blood typing device.

Referring now to FIG. 1A, an exemplary blood typing device 100 is depicted. Device 100 comprises an enclosure 106 having a proximal end 102 and a distal end 104. Enclosure 106 has an elongate hollow structure and can have any suitable cross-sectional shape, including but not limited to circular, ovoid, rectangular, and square cross-sections. In some embodiments, enclosure 106 is at least partially transparent. Enclosure 106 comprises aperture 108 at distal end 104 that is fluidly connected to its hollow interior. In some embodiments, aperture 108 is closeable, such as by a cap or plug. In other embodiments, aperture 108 can include one or more valves positioned along its fluid connection, such as a stopcock.

Enclosure 106 further comprises plunger 110 actuatable within its hollow interior. Plunger 110 is actuatable by its extension out of an opening in the proximal end 102 of enclosure 106. Plunger 110 sealably partitions the hollow interior of enclosure 106 into a distal compartment, positioned between distal end 104 and plunger 110, and a proximal compartment, positioned between plunger 110 and proximal end 102. In some embodiments, the inner surface of enclosure 106 comprises at least a set of first stop 112a and a set of second stop 112b. First stop 112a and second stop 112b are small ridges, bumps, or detents that do not impede the actuation of plunger 110 and do not upset the seal formed by plunger 110 within enclosure 106. However, the presence of first stop 112a and second stop 112b slightly increase the force needed to actuate plunger 110 past them, providing a tactile indicator of predetermined plunger 110 positioning within enclosure 106.

Enclosure 106 further comprises well 114 embedded within its inner surface. Well 114 is recessed into the inner surface of enclosure 106 such that plunger 110 may be actuated over well 114 without touching the inner surface of well 114. In some embodiments, the outer surface of enclosure 106 may include a protrusion to accommodate a recess to form well 114.

The inner surface of well 114 comprises one or more surface regions 116. In some embodiments, the one or more surface regions 116 can each have a population of probes or capture agents. In some embodiments, the probes or capture agents can be immobilized directly on a surface region 116. In other embodiments, the probes or capture agents can be embedded a substrate. The substrate can a porous medium such as a gel matrix or a fibrous strip such as paper, and can enhance the stability and longevity of the probes or capture agents while permitting diffusion of a fluid sample. The probes or capture agents can also be stored in liquid form in breakable capsules or in chambers attached to enclosure 106.

The probes or capture agents can be any suitable molecule, including antibodies, antigens, proteins, and nucleic acids. The probes or capture agents can be configured to capture any desired molecule, including proteins, amines, peptides, antigens, antibodies, nucleic acids, steroids, eicosanoids, DNA sequences, RNA sequences, bacteria, viruses, and fragments thereof. In some embodiments, the probes or capture agents can employ mechanical means for capturing particles, such as magnetic beads for capturing ferromagnetic particles, ferromagnetic beads for capturing magnetic particles, or nanohairs tuned for capturing particles and nanoparticles within a particular size range. In some embodiments, the one or more surface regions 116 can each have a surface treatment capable of bonding or reacting with an ion. The one or more surface regions 116 are thereby suited for capturing any particle of interest for detection and/or analysis.

Figure 2A:
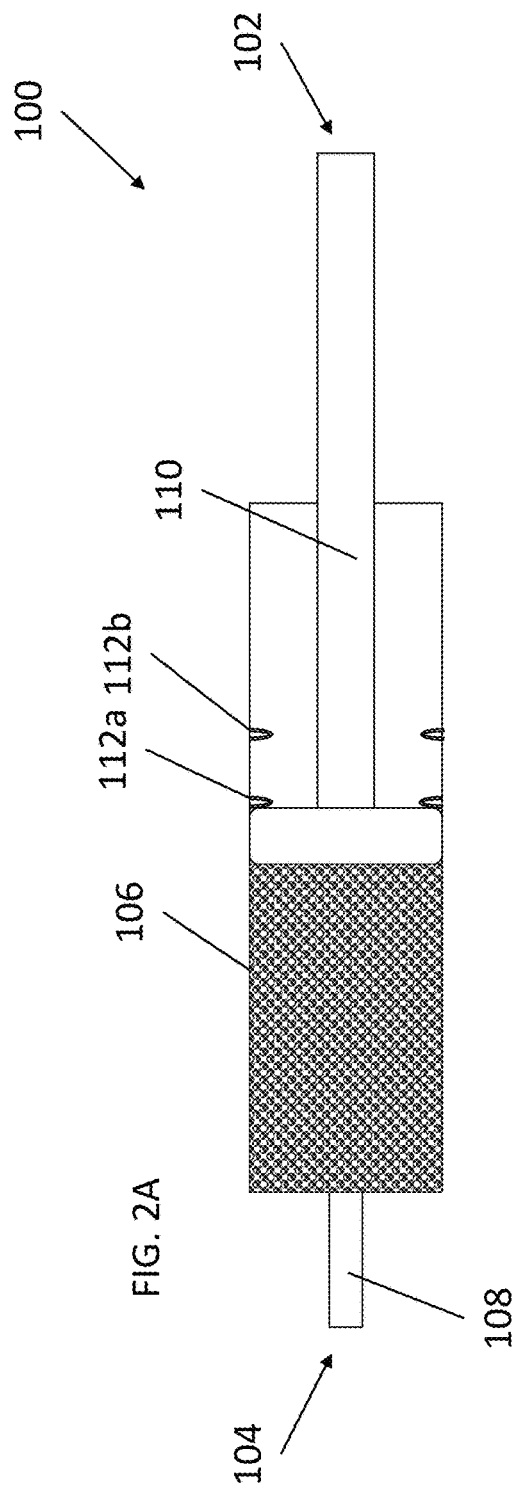
FIG. 2A and FIG. 2B depict the process of loading an exemplary blood typing device with an amount of a sample.
Figure 2B:
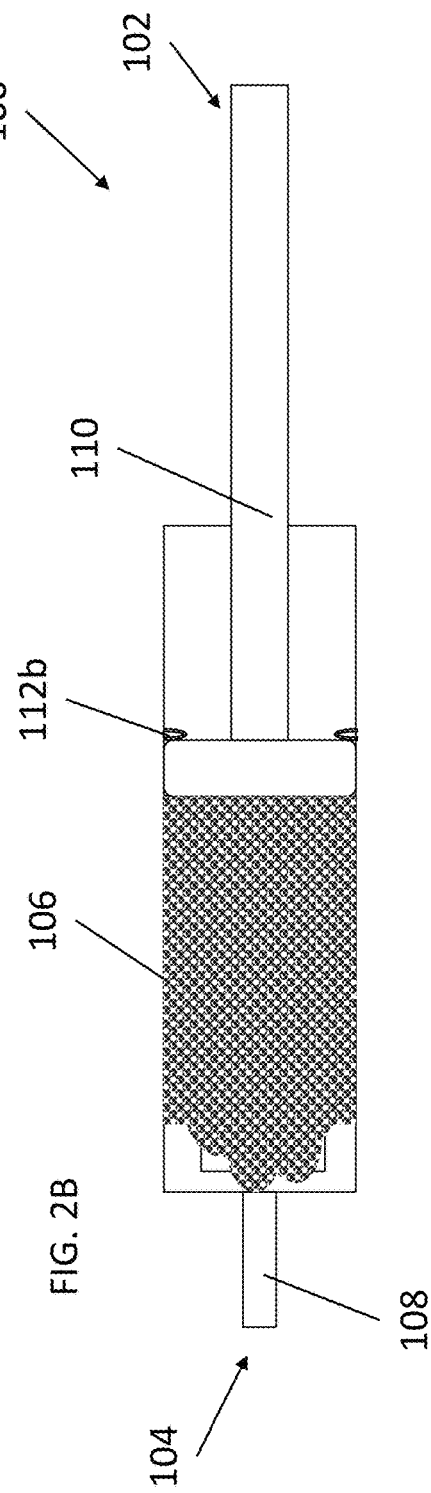

Referring now to FIG. 2A and FIG. 2B, blood typing device 100 is depicted with a blood sample drawn into enclosure 106. It should be understood that while a blood sample is described herein, device 100 is not limited to the analysis of blood. Rather, device 100 is capable of accepting any suitable fluid sample, including but not limited to samples of biological origin, such as saliva, lymph, cerebrospinal fluid, mucus, urine, sweat, and the like, as well as samples of nonbiological origin, such as water samples, rain samples, and chemical compositions. In FIG. 2A, a blood sample has been drawn into enclosure 106 through aperture 108 by actuating plunger 110 in a proximal direction. Actuation of plunger 110 may be halted once plunger 110 meets a set of first stops 112a, indicating that a sufficient amount of blood sample has been drawn. In FIG. 2B, plunger 110 has been actuated an additional step past the set of first stops 112a to rest against a set of second stops 112b to drawn in an amount of air into enclosure 106. The amount of air allows for space in enclosure 106 for the blood sample to be agitated for sufficient coverage on the underlying surface regions 116 of well 114. Agitation can be performed by shaking or squeezing enclosure 106. Optionally, aperture 108 can be closed during agitation to prevent blood sample from spilling out of enclosure 106. After a brief agitation period, such as between about 1 and 2 minutes, the blood sample can be expelled from enclosure 106 by actuating plunger 110 towards aperture 108. In some embodiments, an additional wash buffer can be passed through enclosure 106, such that unbound material can be cleared from device 100 to enhance reading results.

Figure 3:
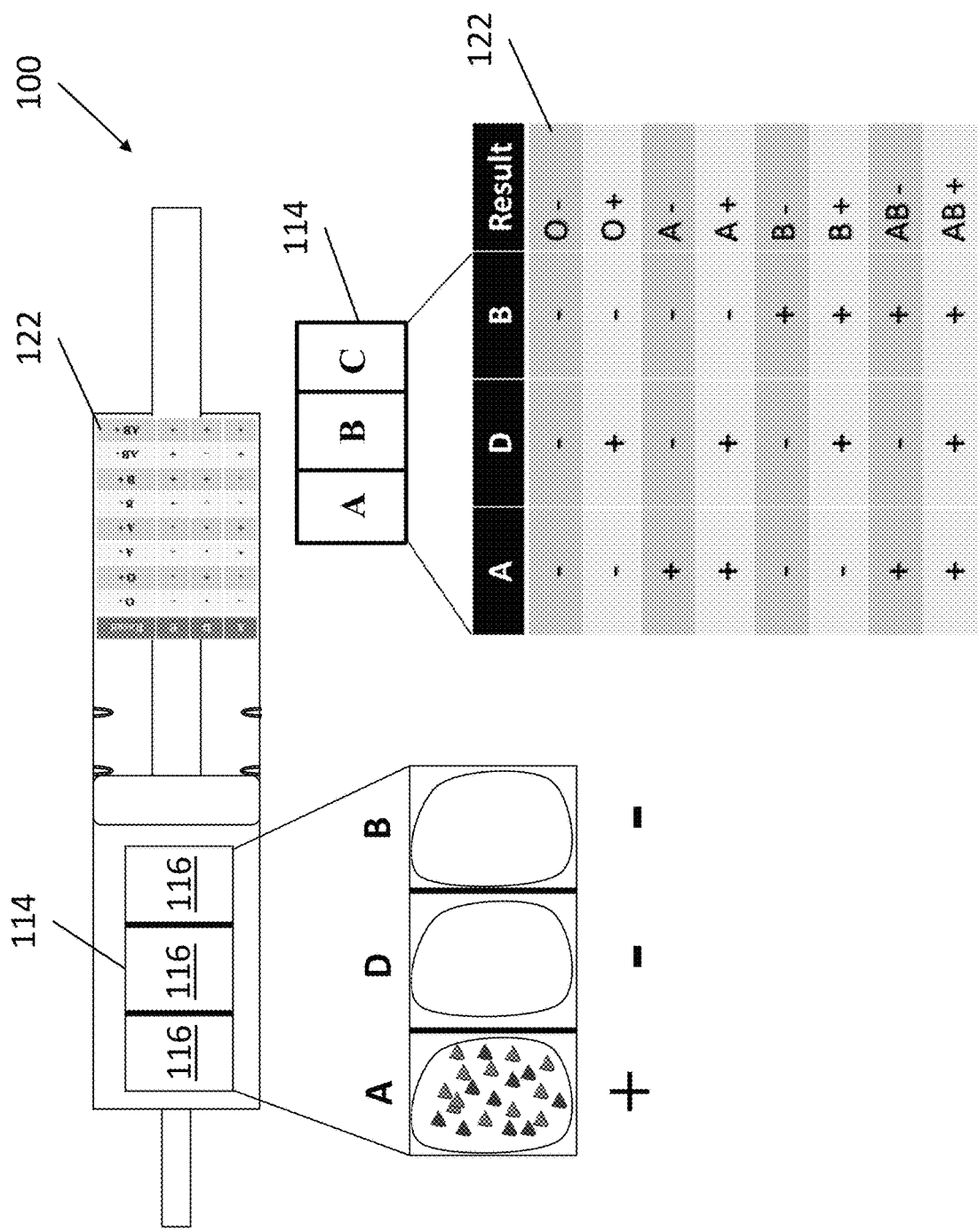
FIG. 3 depicts the process of identifying the content of an analyzed sample by cross-referencing the binding pattern of the surface regions of the well with a chart.

Referring now to FIG. 3, an exemplary blood typing device 100 is depicted after having been exposed to a blood sample. In the depicted device 100, well 114 comprises a first surface region 116 having anti-A antibodies, a second surface region 116 having anti-D antibodies, and a third surface region 116 having anti-B antibodies. The first surface region 116 is thereby configured to bind to RBCs expressing A antigens, the second surface region 116 configured to bind to RBCs expressing Rh antigens, and the third surface region 116 configured to bind to RBCs expressing B antigens. However, it should be understood that well 114 is not limited to the described arrangement, and can have any suitable arrangement of antibodies. The various antibodies can be provided in any suitable amount. For example, each surface region 116 can comprise an amount of antibody between about 10 µL and 100 µL. The various antibodies can be provided in any suitable concentration. For example, the anti-A antibodies can be provided at a titer of 1:64, the anti-D antibodies can be provided at a titer of 1:32, and the anti-B antibodies can be provided at a titer of 1:64.

Successful binding within a surface region 116 can be indicated by agglutination of RBCs on the surface region 116, indicating the presence of a respective blood type and a positive signal. The absence of binding within a surface region 116 is indicated by the lack of agglutination, indicating the absence of a respective blood type and a negative signal. According to chart 122 in FIG. 3, different combinations of positive and negative signals identify the type of blood present in a blood sample. In the depicted example, the first surface region 116 having anti-A antibodies has a positive signal, while the second surface region 116 having anti-D antibodies and the third surface region 116 having anti-B antibodies have negative signals. Referencing chart 122, the blood sample is thereby identified as being A-type blood. For ease of use, chart 122 can be provided with device 100, either as separate paper or electronic documentation, or attached directly to device 100.

In some embodiments, device 100 can be used to draw in at least one additional fluid sample after being exposed to an initial fluid sample. The at least one additional fluid sample can include tags that can be conjugated to the captured particles of interest from the initial fluid sample. The tag can be any material having a detectable physical or chemical property. Such tags have been well-developed in the field of immunoassays and, in general, any tag useful in such methods can be applied to the present invention. Thus, a tag is any composition detectable by spectroscopic, photochemical, biochemical, immunochemical, electrical, optical or chemical means.

Means of detecting tags are well known to those of skill in the art. Thus, for example, where the tag is a radioactive label, means for detection include a scintillation counter or photographic film as in autoradiography. Where the tag is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic tags may be detected by providing appropriate substrates for the enzyme and detecting the resulting reaction product. Finally, simple colorimetric tags may be detected simply by observing the color associated with the tag.

Figure 4:
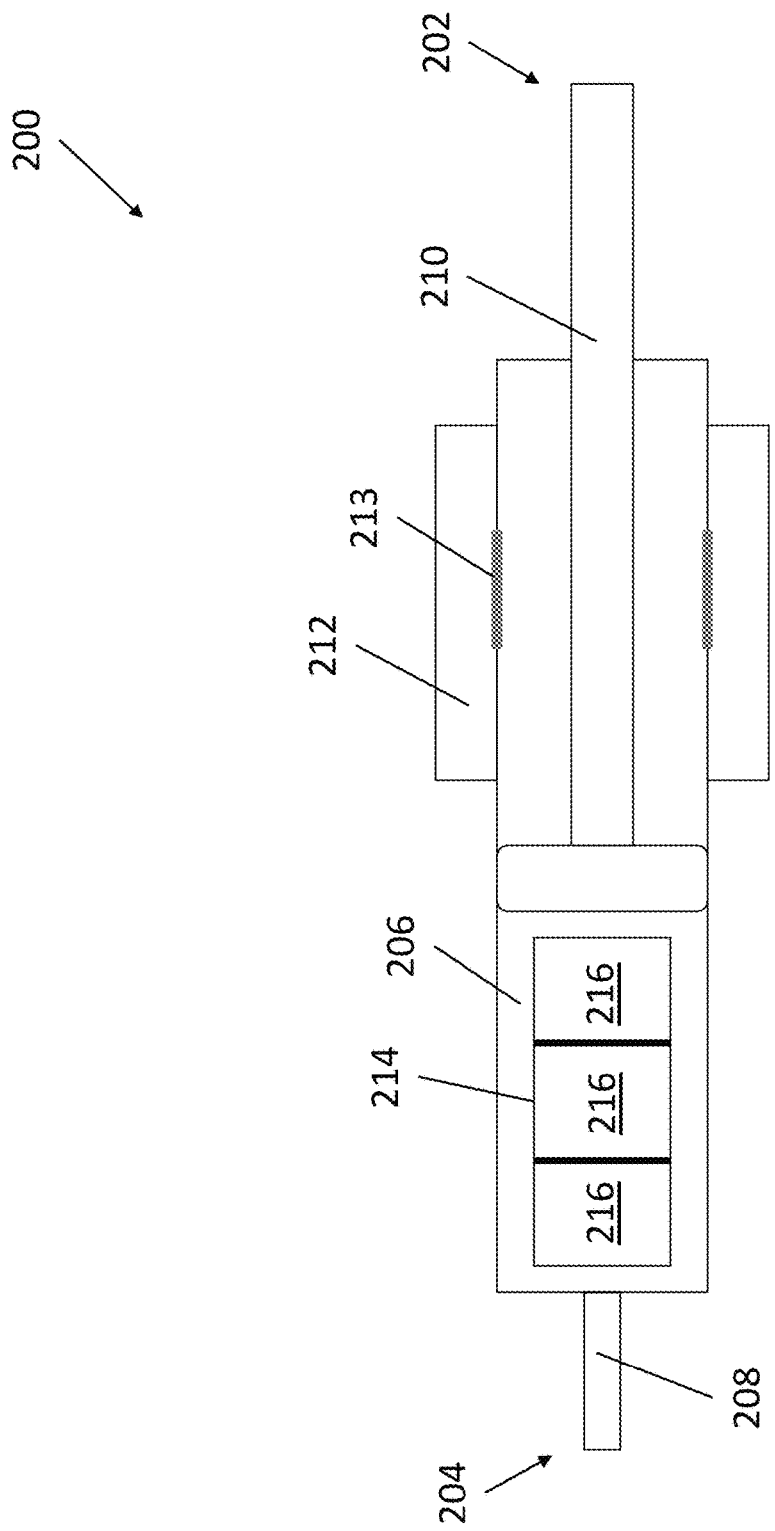
FIG. 4 depicts another exemplary blood typing device having side chambers.

Referring now to FIG. 4, an alternative blood typing device 200 is depicted. Similarly to device 100, device 200 comprises an enclosure 206 having a proximal end 202 and a distal end 204, an aperture 208, a plunger 210, and a well 214 having one or more surface regions 216. Device 200 can also include any suitable modifications, including a light source, magnifying lens, sensor, electrode array, and the like. Device 200 further comprises one or more side chambers 212 positioned proximal to well 214. The one or more side chambers 212 are fluidly connected to the hollow interior of enclosure 206 by chamber opening 213. In some embodiments, chamber opening 212 can comprise a flap or sliding door that is openable by actuating plunger 210 in a proximal direction.

Figure 5A:
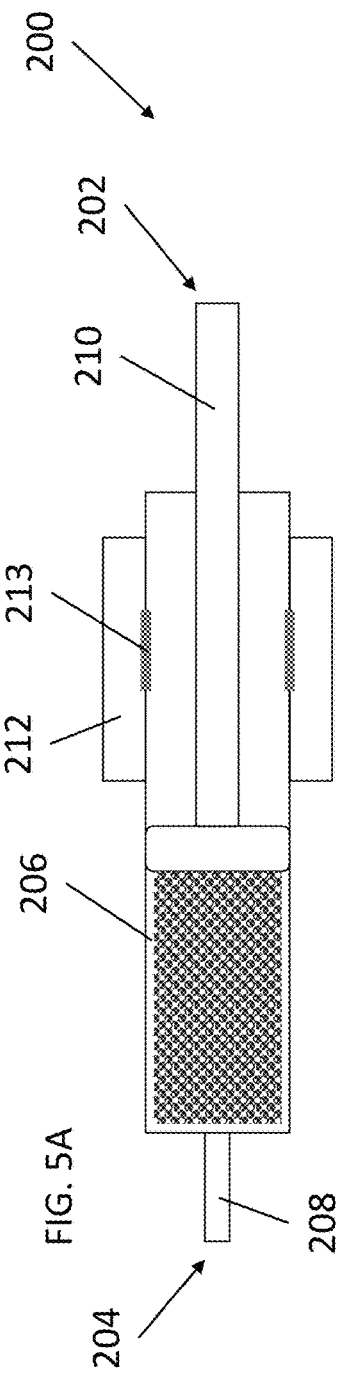
FIG. 5A through FIG. 5C depict the sequential steps of using the exemplary blood typing device depicted in FIG. 4.
Figure 5B:
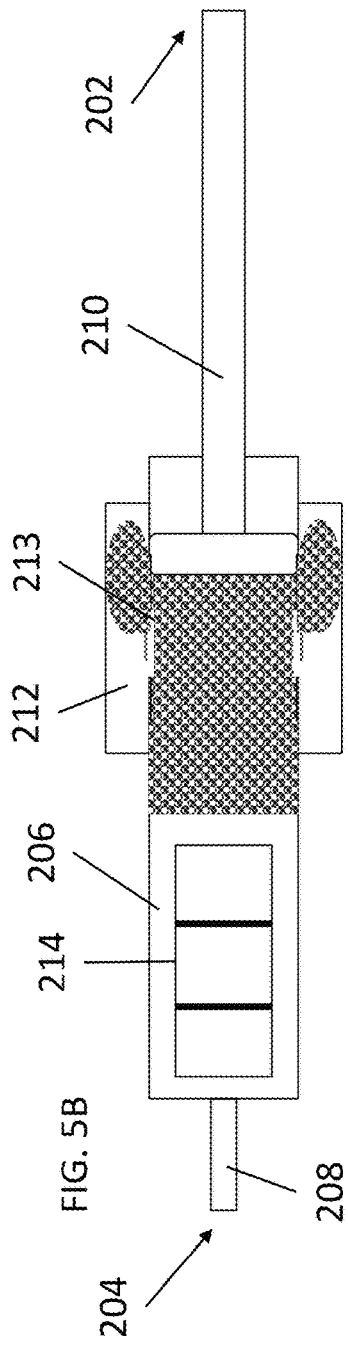
Figure 5C:
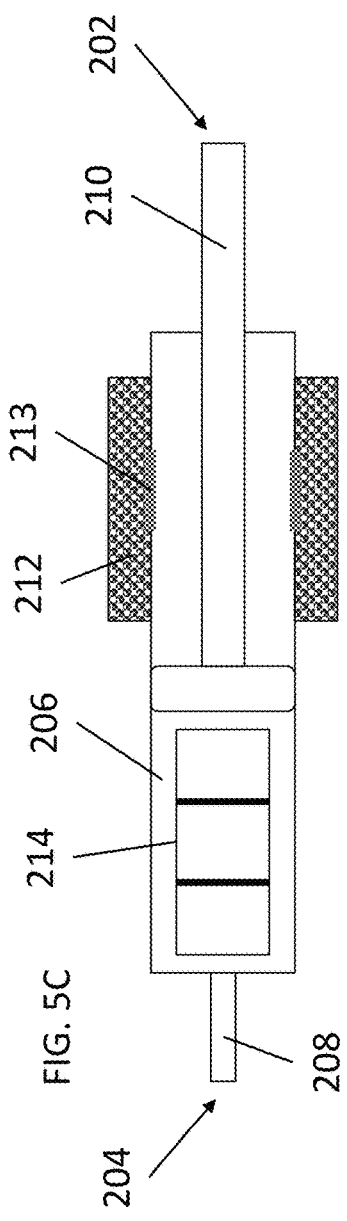

Referring now to FIG. 5A through FIG. 5C, the function of side chambers 212 is described. Beginning with FIG. 5A, device 200 is capable of accepting a fluid sample in a manner similar to device 100, as described elsewhere herein. After agitating the fluid sample within enclosure 206, plunger 210 may be actuated further in a proximal direction, exposing the fluid sample to chamber openings 213 and permitting the fluid sample to enter side chambers 212 in FIG. 5B. Once the fluid sample has been fully contained in side chambers 212, plunger 210 may be actuated in a distal direction to separate the fluid sample from well 214. In this manner, the fluid sample is contained within device 200 for later analysis or processing, or for convenient and clean disposal.

Figure 6:
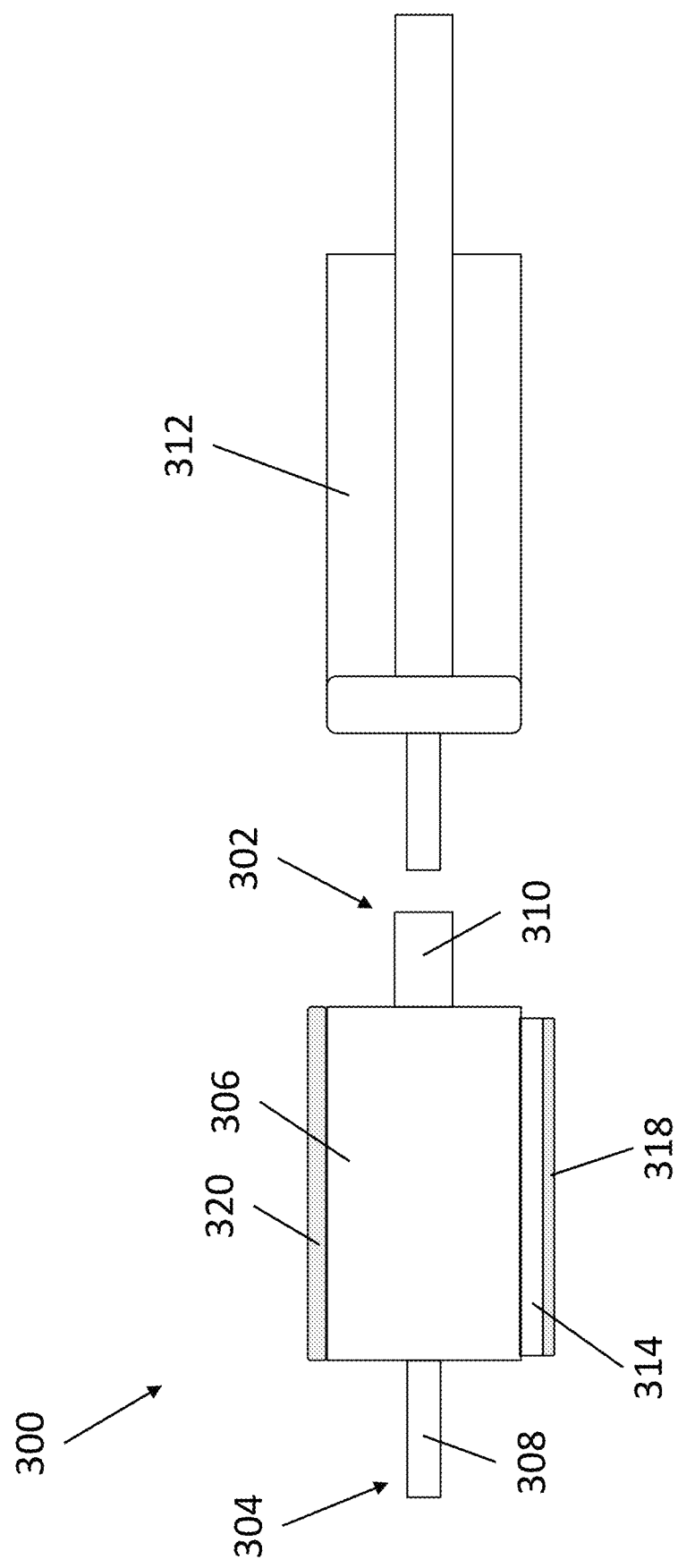
FIG. 6 depicts another exemplary blood typing device that is separable from a syringe component.

In another example, FIG. 6 depicts an alternative blood typing device 300. Similarly to device 100, device 300 comprises an enclosure 306 having a proximal end 302 and a distal end 304, a distal aperture 308, and a well 314 having one or more surface regions 316 (not visible). Device 300 can also include any suitable modifications, including a light source 318, magnifying lens, sensor 320, electrode array, and the like. Device 300 further comprises a proximal aperture 310 fluidly connected to the hollow interior of enclosure 306. Proximal aperture 310, like distal aperture 308, can be closeable such as by a cap or plug, and include one or more valves positioned along its fluid connection, such as a stopcock. Distal aperture 308 and proximal aperture 310 are each connectable to syringe 312. Syringe 312 can be any suitable syringe commonly used in the art. Fluid samples can be injected into or removed from enclosure 306 directly from syringe 312. Fluid samples can also be injected into or removed from enclosure 306 by connecting syringe 312 to distal aperture 308 or proximal aperture 310 and manipulating fluid samples through the opposing proximal aperture 310 or distal aperture 308, respectively, using syringe 312.

Figure 7A:
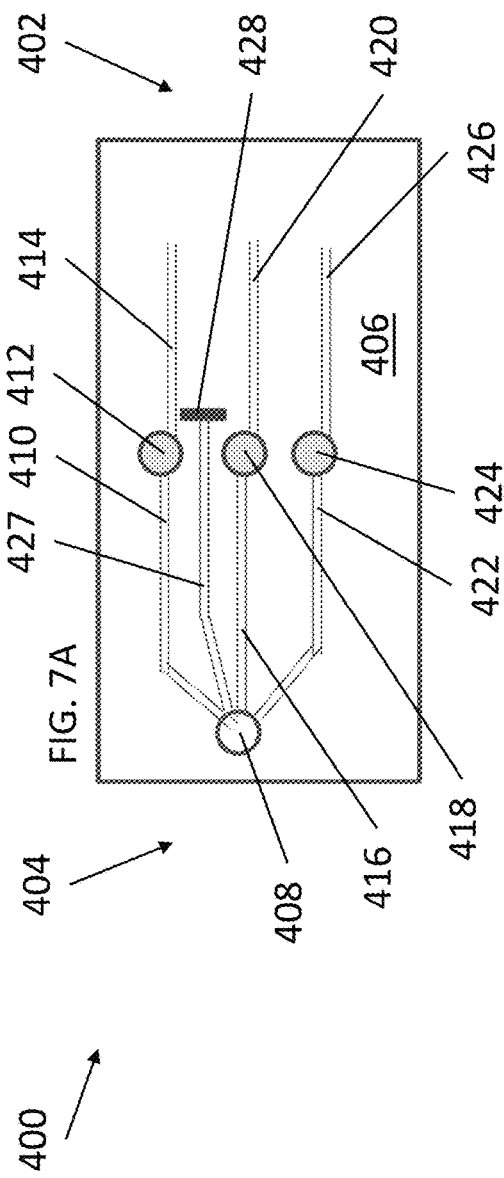
FIG. 7A through FIG. 7C depict another exemplary blood typing device having capillary tubes.
Figure 7B:
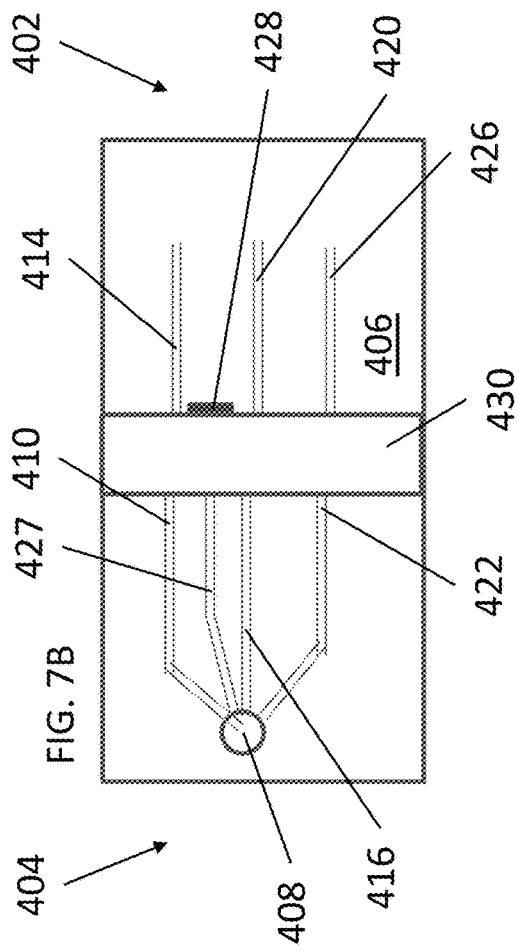
Figure 7C:
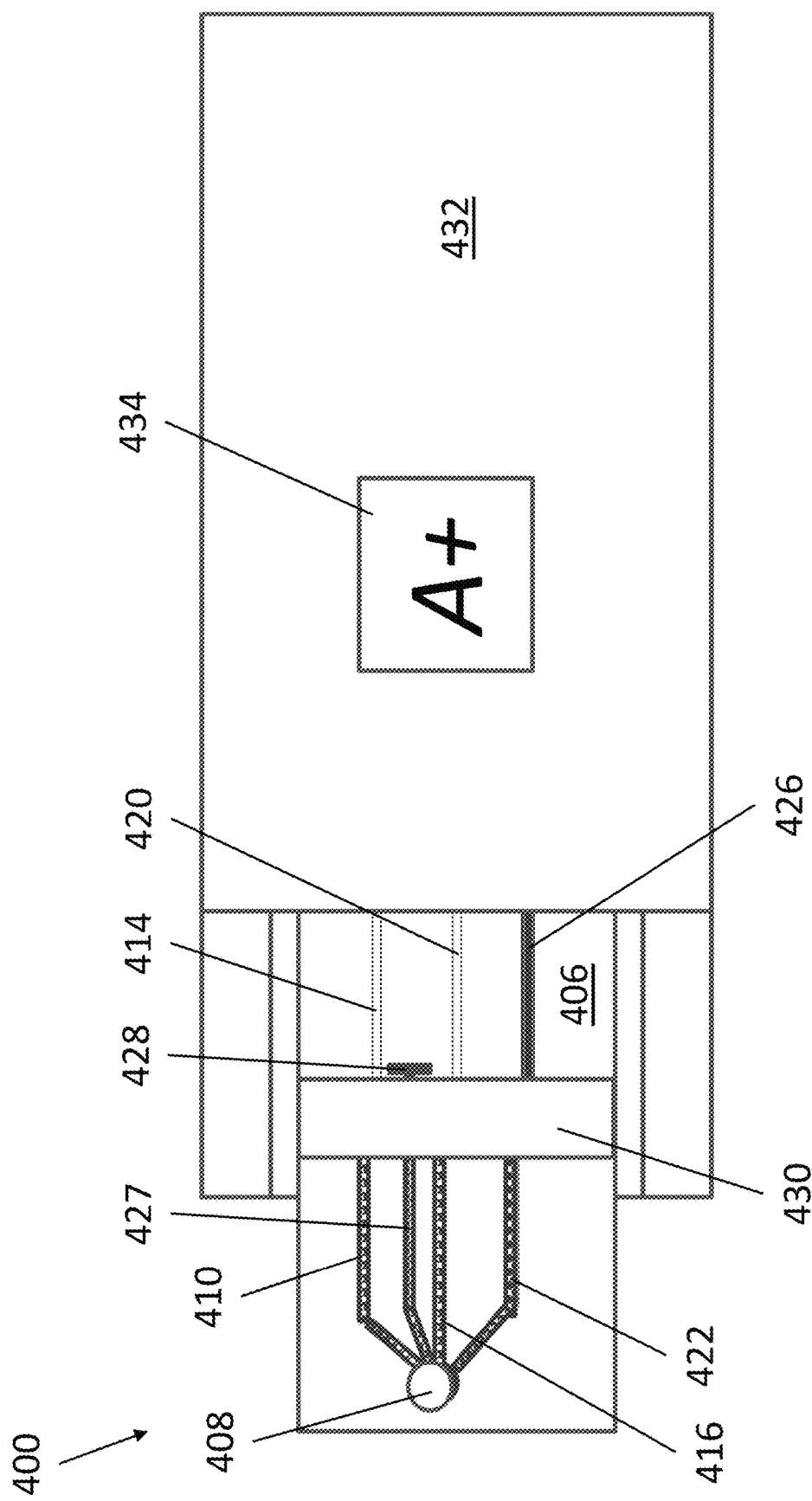

In another example, FIG. 7A through FIG. 7C depict an alternative blood typing device 400. Device 400 comprises an enclosure 406 having a proximal end 402 and a distal end 404. Enclosure 406 comprises an aperture 408 fluidly connected to one or more capillary tubes and wells. For example, in the embodiment depicted in FIG. 7A, device 400 comprises an aperture 408 fluidly connected to a first proximal capillary tube 410, a second proximal capillary tube 416, and a third proximal capillary tube 422. Each proximal capillary tube 410, 416, and 422 is fluidly connected to a first well 412, a second well 418, and a third well 424, respectively. Each of the wells can include a surface region having a population of immobilized probes or capture agents comprising any suitable molecule, including antibodies, antigens, proteins, and nucleic acids, as described elsewhere herein. Each well 412, 418, and 424 is fluidly connected to a first distal capillary tube 414, a second distal capillary tube 420, and a third distal capillary tube 426, respectively. In various embodiments, device 400 can further comprise one or more small air holes connected to the various capillary tubes and wells, wherein the air holes permit air transfer as fluid sample moves within device 400 by capillary action without leaking any fluid sample.

In some embodiments, a removable barrier is provided in the fluid connection between each well and a fluidly connected distal capillary tube. The removable barrier allows a user to control the flow of a fluid from well 412, 418, and 424 into distal capillary tube 414, 420, and 426, respectively. The removable barrier can be toggled by barrier breaker 430, wherein barrier breaker 430 can remove the barrier by any suitable means, such as breaking the barrier, sliding the barrier away, or opening an aperture in the barrier. In some embodiments, device 400 further comprises indicator well 428 fluidly connected to aperture 408 by capillary tube 427. Indicator well 428 can be positioned proximal to barrier breaker 430, such that in certain embodiments wherein barrier breaker 430 occludes wells 412, 418, and 424 from view, indicator well 428 can also receive an amount of a fluid sample, showing that the flow of the fluid sample has reached wells 412, 418, and 424. In some embodiments, indicator well 428 can include a probe or capture agent that changes color or fluoresces in response to contact with a fluid sample to enhance its indication.

Referring now to FIG. 7C, device 400 is depicted with a fluid sample inserted into a reader 432. A fluid sample can be introduced into aperture 408 by any suitable manner, such as with a syringe or with a pin prick. The fluid sample travels by capillary action through proximal capillary tubes 410, 416, 422, and 427. The fluid sample reaches indicator well 428, which shows that the fluid sample has also reached wells 412, 418, and 424 (which are occluded from view by barrier breaker 430). The fluid sample can be given a period of time to incubate within each of wells 412, 418, and 424. Device 400 can also be agitated to increase the amount of contact between the fluid sample and the probes or capture agents within wells 412, 418, and 424. Barrier breaker 430 can be toggled to permit the flow of fluid from wells 412, 418, and 424 into distal capillary tubes 414, 420, and 426, respectively. Reader 432 is able to read the status of distal capillary tubes 414, 420, and 426, such as the presence or absence of fluid, the color of fluid, the temperature of the fluid, the fluorescence of the fluid, the flow rate of the fluid, counting the number of particles in the fluid, and the like. Reader 432 is also able to identify the contents of the fluid sample based on the status of the distal capillary tubes, whereupon the identity of the contents of the fluid sample can be displayed on digital display 434.

In the exemplary embodiment shown in FIG. 7C, the fluid sample is whole blood, and the capture agents within well 412, 418, and 424 are anti-A antibodies, anti-D antibodies, and anti-B antibodies, respectively. As described elsewhere herein, RBCs may bind or agglutinate within a well when exposed to a matching capture agent, indicating a positive signal. RBCs may also fail to bind or agglutinate within a well when there are no matching capture agents, indicating a negative signal. Agglutination within a well impedes the flow of fluid, leading to minimal fluid travel into the distal capillary tubes to indicate a positive signal. Lack of agglutination within a well does not impede the flow of fluid, leading to fluid travel into the distal capillary tubes to indicate a negative signal. In FIG. 7C, first distal capillary tube 414 and second distal capillary tube 420 are empty, indicating that agglutination has occurred in first well 412 (positive for A-type blood) and second well 418 (Rh positive). Third distal capillary tube 426 is filled with fluid, indicating that no agglutination has occurred in third well 424 (negative for B-type blood). Reader 432 detects the absence or presence of fluid within the distal capillary tubes, and displays an unambiguous identification of the blood type on digital display 434.

It should be understood that the several features of the blood typing devices of the present invention can be rearranged or modified without altering their function to accommodate different orientations and configurations. For example, in some embodiments the enclosure of the device can be divided into individual chambers, each chamber having distinct wells and surface regions to prevent mixing between chambers. The individual chambers can be connected by channels to route a sample fluid into distinct chambers for different purposes, such as a mixing chamber, a reacting chamber, and a viewing chamber. In some embodiments, the wells or surface regions can be shaped to identify the contents of the wells or surface regions. For example, a well having anti-A antibodies can be shaped like the letter "A", a well having anti-D antibodies can be shaped like the letter "D" or the symbol "+", and a well having anti-B antibodies can be shaped like the letter "B". In some embodiments, the wells or surface regions can be directly labeled with the contents of the wells or surface regions.

The various blood typing devices of the present invention are amenable to any suitable modification to augment their function. For example, blood typing devices can further comprise light sources, such as in FIG. 1B. Light source 118 is positioned adjacent to well 114 and is configured to project light through well 114. Surface regions 116 that have captured one or more particles of interest occlude light passing through well 114. In this manner, the presence of any particles of interest on a surface region 116 can be determined based on the intensity of light shining through well 114. In some embodiments, the blood typing devices can comprise a magnifying lens on the surface of an enclosure opposing a well, such that visualization of captured particles on surface regions within the well is enhanced. In some embodiments, the blood typing devices can comprise a partially transparent or translucent graphic or chart on the surface of an enclosure opposing a well, wherein the graphic or chart is labeled and partitioned to mirror the one or more surface regions within the well. Light shining through a well can be projected onto the graphic or chart, thereby providing a quick reference indicating which surface region has captured particles, as well as the identity of the captured particles.

Figure 1B:
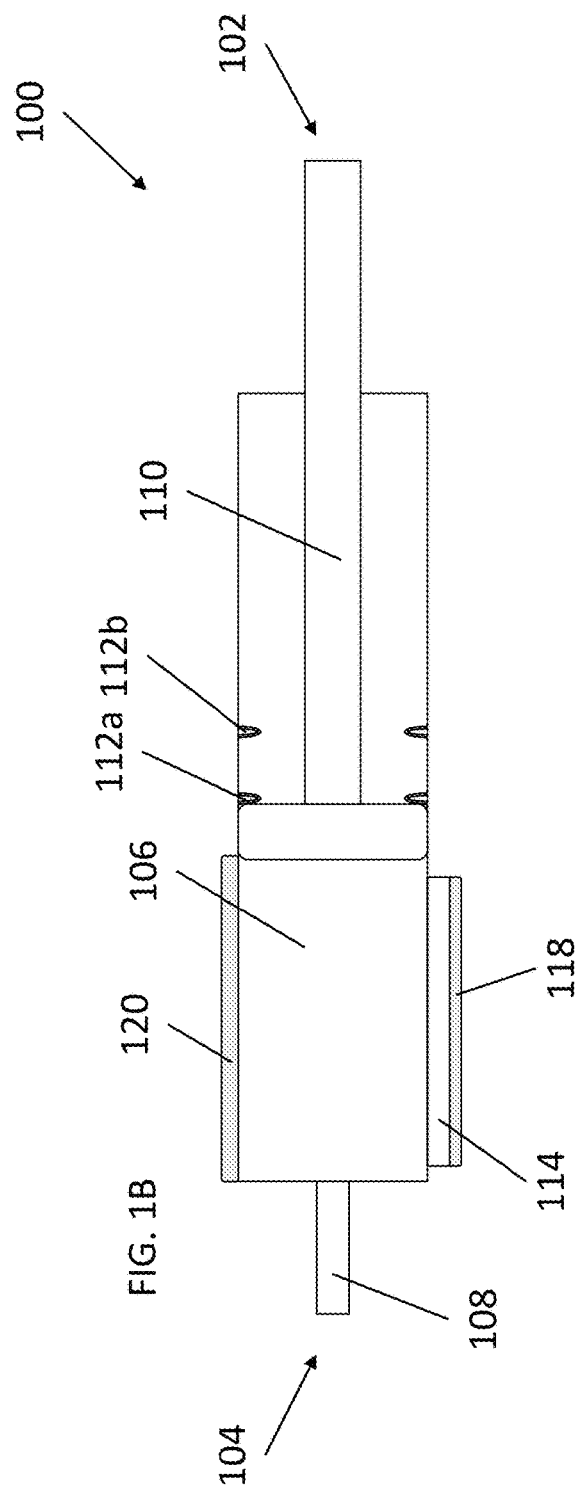
FIG. 1B depicts a side view of an exemplary blood typing device.

In some embodiments, the blood typing devices can comprise sensors positioned on the surface of an enclosure opposing a well, such as in FIG. 1B. Light shining through well 114 can be detected by sensor 120, which can be supplemented with a computing unit or CPU and a digital readout to display a positive or negative reading for a particle of interest or to quantify the amount of captured particle based on the intensity of light. In some embodiments, the blood typing devices can comprise an electrode array embedded in a well (not pictured). An electrode array can also be supplemented with a computing unit or CPU and a digital readout to amperometrically detect the presence or quantify the amount of particles captured by a surface region as a measure of impedance. In various embodiments, the computing unit or CPU can be linked to the digital readout by a wired or wireless connection. The digital readout can be incorporated onto a blood typing device, or be on a separate device, such as a desktop, a laptop, a tablet, a cellular phone, a smartphone, or any other device as would be understood by those skilled in the art. In some embodiments, the computing unit or CPU can be located on the separate device, wherein a blood typing device may be inserted into a compatible slot on the separate device and is readable by the separate device like a chip.

The blood typing devices of the present invention can be made using any suitable method known in the art. The method of making may vary depending on the materials used. For example, components of the device comprising a metal may be milled from a larger block of metal or may be cast from molten metal. Likewise, components of the device substantially comprising a plastic or polymer may be milled from a larger block or injection molded. In some embodiments, the devices may be made using 3D printing or other additive manufacturing techniques commonly used in the art.

Method of Use

The present invention also provides methods of determining blood type from a sample of blood. The methods use the portable blood typing devices described herein, the devices having at least one well with a first surface region containing anti-A antibodies, a second surface region containing anti-D antibodies, and a third surface region containing anti-B antibodies.

In various embodiments, the methods begin with a first step of providing a portable blood typing device of the present invention. In a second step, a blood sample is drawn into the first chamber and the at least one well of the provided portable blood typing device. The blood sample can be drawn in any suitable manner, such as by actuating the plunger of the provided portable blood typing device in a proximal direction, the blood sample being drawn directly from a subject, such as with a needle, or from a reservoir of blood. The blood sample can also be placed in the first chamber from an external source, such as with a separate syringe. In a third step, the blood sample is agitated within the first chamber and the at least one well of the provided portable blood typing device. In a fourth step, the plunger of the provided portable blood typing device is actuated to eject the blood sample from the provided portable blood typing device. Depending on the device provided, the plunger can be actuated in a distal direction to eject the blood sample from the first chamber, or the plunger can be actuated in a further proximal direction to sequester the blood sample in a proximally located enclosure or to draw the blood sample into a removable syringe for removal. In a fifth step, the presence of agglutination in the first surface region, the second surface region, and the third surface region of the provided portable blood typing device is recorded.

As described elsewhere herein, the blood type of a sample of blood can be determined based on the agglutination of the first surface region, the second surface region, and the third surface region. For example, in a first combination, the presence of agglutination in the first surface region and the absence of agglutination in the third surface region indicates the blood sample contains A-type blood. In a second combination, the presence of agglutination in the third surface region and the absence of agglutination in the first surface region indicates the blood sample contains B-type blood. In a third combination, the presence of agglutination in the first surface region and the third surface region indicates the blood sample contains AB-type blood. In a fourth combination, the absence of agglutination in the first surface region and the third surface region indicates the blood sample contains O-type blood. In any of the first, second, third, and fourth combinations, the presence of agglutination in the second surface region indicates the blood sample is Rh positive, and the absence of agglutination in the second surface region indicates the blood sample is Rh negative.

In certain embodiments, the provided portable blood typing device comprises extra functionality that may require additional method steps. For example, the provided portable blood typing device may comprise a light source, whereupon the fifth step can be preceded by a step of activating the light source to facilitate the recordation of agglutination in a surface region. In another example, the provided portable blood typing may comprise a sensor or electrode array configured to detect agglutination in a surface region, whereupon the fifth step can be preceded by a step of activating the sensor or electrode array, and the fifth step of recording the presence of agglutination may be performed on a smartphone or other device coupled to the sensor or electrode array by a wired or wireless connection.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1. Prototyping of Blood Typing Devices

Figure 9:
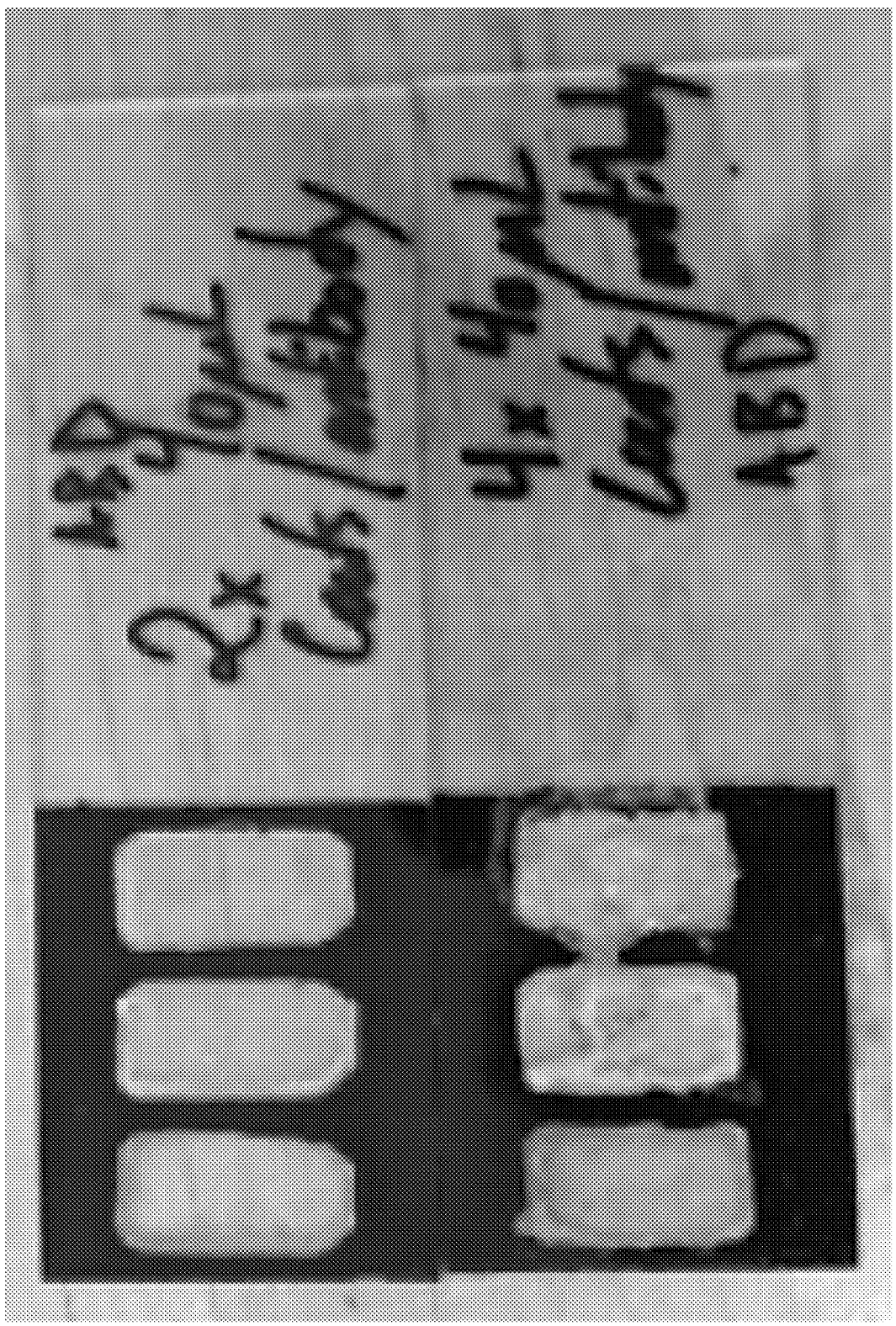
FIG. 9 depicts the results of experimental prototyping of a glass slide coating procedure. Slides were coated with antibodies in the order of anti-A, anti-B, and anti-D, from left to right. The top slide has 2×40 µL coats of each antibody, the bottom slide has 4×40 µL coats of each antibody. 45 minutes of dry time passed between each coat.

Antibody applications and shell designs and were prototyped in the course of device development. While antibodies are usually kept in liquid form, for the purposes of the device, antibodies were dried onto a plastic resin and rehydrated by a blood sample. To prevent the antibodies from detaching after being rehydrated, antibodies can be covalently bonded, chemically coated, or immobilized or fixed by any other commonly used means to a well surface. Referring now to FIG. 8A through FIG. 8D, the binding characteristics of antibody coatings are shown. Positive signals were indicated by agglutination of red blood cells (FIG. 8A, FIG. 8B). Negative signals were indicated by the absence of agglutination of red blood cells (FIG. 8C, FIG. 8D). Referring now to FIG. 9, the results of antibody coatings tested on glass slide surfaces are shown. The top row shows a double layer of antibody coatings, 40 µL per layer. The bottom row shows a four layer antibody coating, 40 µL per layer. Each layer was allowed to dry for 45 minutes before applying a successive layer.

Figure 14A:
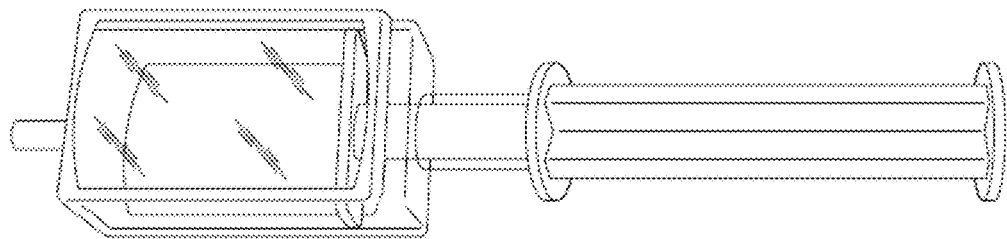
FIG. 14A through FIG. 14D depict an exemplary compact prototype blood typing device. Computer-aided design models of the prototype device are shown in FIG. 14A (perspective view), FIG. 14B (perspective view of the device shell), and FIG. 14C (perspective view of the device well tray).
Figure 14B:
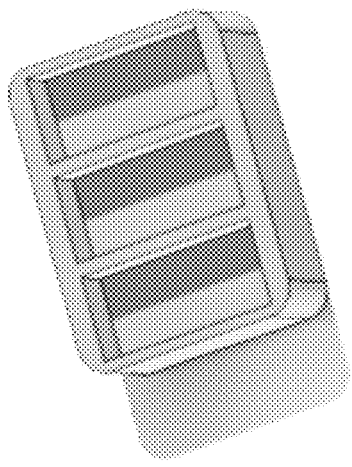
Figure 14C:
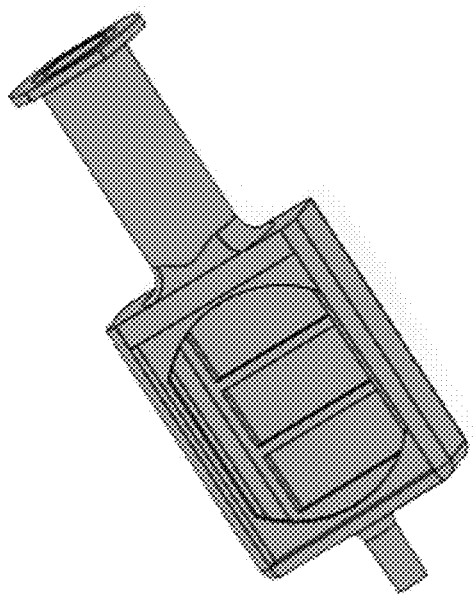
Figure 14D:
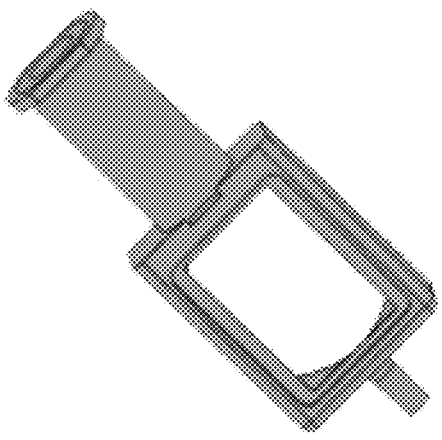

Referring now to FIG. 10A through FIG. 10D, a prototype blood typing device having a rectangular shape is shown. The prototype device has an integrated rectangular plunger with a standard syringe tip. Referring now to FIG. 11A through FIG. 11C and FIG. 12A through FIG. 12D, prototype blood typing devices are shown having a magnifying lens and stop bumps/detents. The magnifying lens improves the ease of examining the wells. The stop bumps/detents provide tactile feedback for various positions of the plunger (shown in FIG. 13A through FIG. 13C). The plunger also includes two rubber rings for an enhanced fit and seal. Referring now to FIG. 14A through FIG. 14D, a compact prototype blood typing device is shown having a rounded plunger barrel and a removable well tray. FIG. 15A through FIG. 14C depict the use of the compact prototype device with a loaded well tray and a test blood sample. Referring now to FIG. 16A through FIG. 16C, a compact prototype blood typing device is shown with a luer lock aperture compatible with commonly used syringes. The prototype device includes upper and lower slots capable of receiving removable glass slides to seal the blood sample chamber. The prototype device accepts glass slides having surface regions with anti-A, anti-B, and anti-D antibody coatings.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A portable blood typing device comprising:
   an enclosure having a proximal end, a distal end, and a hollow interior;
   an actuatable plunger positioned within the enclosure, the plunger dividing the hollow interior into a first distal chamber and a second proximal chamber;
   a closeable aperture on the distal end of the enclosure providing access to the first chamber; and
   at least one well embedded in the enclosure;
   wherein the at least one well comprises at least three distinct surface regions, each surface region comprising a probe that binds to a distinct antigen, a first surface region coated in a first probe that binds to antigen A, a second surface region coated in a second probe that binds to antigen D, and a third surface region coated in a third probe that binds to antigen B.

2. The portable blood typing device of claim 1, wherein the first probe is anti-A antibody, the second probe is anti-D antibody, and the third probe is anti-B antibody.

3. The portable blood typing device of claim 1, wherein the at least one well extends outward from the first chamber such that actuation of the plunger within the enclosure does not touch the first surface region, the second surface region, or the third surface region of the at least one well.

4. The portable blood typing device of claim 1, wherein the enclosure comprises at least one hard stop or detent on its inner surface that stops the plunger in at least a first distal position and at least a second proximal position.

5. The portable blood typing device of claim 1, wherein the enclosure is at least partially transparent.

6. The portable blood typing device of claim 1, further comprising a magnifying lens positioned on the enclosure opposite from the at least one well, the magnifying lens capable of magnifying the first surface region, the second surface region, and the third surface region.

7. The portable blood typing device of claim 1, wherein the enclosure is at least partially squeezable.

8. The portable blood typing device of claim 1, further comprising a light source positioned on the enclosure adjacent to the at least one well, the light source capable of projecting light through the first surface region, the second surface region, and the third region, and onto a translucent surface positioned opposite from the at least one well.

9. The portable blood typing device of claim 1, further comprising at least one side chamber fluidly connected to the hollow interior of the enclosure, the fluid connection being positioned near the proximal end of the enclosure.

10. The portable blood typing device of claim 1, wherein the enclosure can split into at least two pieces, such that the plunger and the second chamber are separable from the first chamber.

11. The portable blood typing device of claim 1, further comprising a blood typing chart attached to the enclosure, the blood typing chart relating a positive or a negative reading in the first surface region, the second surface region, and the third surface region to a blood type.

12. The portable blood typing device of claim 1, further comprising a sensor electronically connected to a CPU and a display, wherein the sensor automatically detects a positive or negative signal on each of the surface region, the CPU assigns a blood type based on the detected signals, and the display shows the blood type.

13. The portable blood typing device of claim 12, wherein the sensor is selected from the group consisting of: a light sensor, an impedance sensor, and a color sensor.

14. The portable blood typing device of claim 12, wherein the sensor is readable by a smartphone.

15. A method of blood typing, comprising the steps of:
providing the portable blood typing device of claim 1;
actuating the plunger in a proximal direction to draw an amount of a blood sample into the first chamber and the at least one well;
agitating the blood sample within the first chamber and the at least one well;
actuating the plunger in a distal direction to eject the blood sample from the first chamber; and
recording the presence of agglutination in the first surface region, the second surface region, and the third surface region.

16. The method of claim 15, wherein
the presence of agglutination in the first surface region and the absence of agglutination in the third surface region indicates that the blood sample comprises A-type blood;
the absence of agglutination in the first surface region and the presence of agglutination in the third surface region indicates that the blood sample comprises B-type blood;
the presence of agglutination in the first surface region and the presence of agglutination in the third surface region indicates that the blood sample comprises AB-type blood;
the absence of agglutination in the first surface region and the absence of agglutination in the third surface region indicates that the blood sample comprises O-type blood;
the presence of agglutination in the second surface region indicates that the blood sample comprises Rh positive blood; and
the absence of agglutination in the second surface region indicates that the blood sample comprises Rh negative blood.

17. The method of claim 15, wherein the step of recording the presence of agglutination in the first surface region, the second surface region, and the third surface region is performed by a smartphone.

* * * * *